US00PP11839P2

(12) United States Plant Patent
Zary

(10) Patent No.: US PP11,839 P2
(45) Date of Patent: Apr. 24, 2001

(54) FLORIBUNDA ROSE PLANT NAMED 'JACAMQUE'

(75) Inventor: Keith W. Zary, Thousand Oaks, CA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 0 days.

(21) Appl. No.: 09/266,991

(22) Filed: Mar. 12, 1999

(51) Int. Cl.[7] ..... A01H 5/00
(52) U.S. Cl. ..... Plt./145
(58) Field of Search ..... Plt./141, 145, 146

*Primary Examiner*—Howard J. Locker
(74) *Attorney, Agent, or Firm*—Klarquist Sparkman Campbell Leigh & Whinston, LLP

(57) ABSTRACT

A floribunda rose plant having a compact plant habit; dark green, glossy, disease-resistant foliage; abundant amber flowers; good clustering ability; and rapid rebloom.

1 Drawing Sheet

The present invention relates to a new and distinct variety of rose plant of the floribunda class which was originated by me by crossing the variety 'JACrun', (not patented, 'JACjem', U.S. Plant Pat. No. 5,001×'JACdew', U.S. Plant Pat. No. 5,122), with the variety 'HARroony', U.S. Plant Pat. No. 5,582.

The primary objective of this breeding was to produce a new rose variety having the compact, well-branched plant habit, and dark green, glossy, disease-resistant foliage, abundant flowers, good clustering ability and rapid rebloom of the female parent and the fragrance, vigor, large flowers and amber color of the male parent. The objective was substantially achieved, along with other desirable improvements, as evidenced by the following unique combination of characteristics that are outstanding in the new variety and that distinguish it from its parents, as well as from all other varieties of which I am aware:

1. Medium-sized, fragrant flowers.
2. Compact plant habit.
3. Glossy, dark-green, disease resistant foliage.
4. A light amber flower color.
5. Rapid rebloom.
6. Flowers presented in clusters.

'JACamque' is a vigorous, compact well-branched floribunda garden rose. As flowers open, eyes below the flower buds break rapidly, creating a new crop of flowers. This insures the plant is almost always in flower.

Asexual reproduction of this new variety by budding, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is resonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—'JACrun', (not patented, 'JACjem', U.S. Plant Pat. No. 5,001×'JACdew', U.S. Plant Pat. No. 5,122).

*Pollen parent.*—'HARroony', U.S. Plant Pat. No. 5,582.

Classification:

*Botanical.*—*Rosa hybrida.*

*Commercial.*—Floribunda.

FLOWER

Observations made from specimens grown in a garden environment at Somis, Calif. in March 1997 to November 1998.

Blooming habit: Recurrent.

Bud:

*Size.*—1¼ inches long when the petals start to unfurl.

*Form.*—The bud form is long, pointed ovoid.

*Color.*—When sepals first divide, bud color is Yellow-Orange Group 18B with some Red Group 44D on petal edges and tips. When half blown, the upper sides of the petals are Yellow-Orange Group 18B with faint Red Group 44D on petal edges and tips;

*Sepals.*—Color: Green Group 138B. Surface texture: Covered in fine hairs. There are three normally appendaged sepals. There are two unappendaged sepals with hairy edges.

*Receptacle.*—Color: Green Group 137D. Shape: Funnel. Size: Small, about 5/16×¼ inch. Surface: Smooth.

*Peduncle.*—Length: Short, averaging about 2½ inches. Surface: Glandular. Color: Yellow Green Group 146D. Strength: Stiff, erect.

Bloom:

*Size.*—Medium. Average open size is about 3½ inches.

*Borne.*—Several together in clusters of three to five blooms having rounded shape.

*Stems.*—Strength: Strong. Average length is about 12 to 14 inches long.

*Form.*—When first open: High-centered. Permanence: Flattens, all petals curl.

*Petalage.*—Number of petals under normal conditions: 25.

*Color.*—The upper sides of the petals are Yellow-Orange Group 18B with faint Red Group 44D on petal edges and tips. The reverse sides of the petals are Yellow-Orange Group 18B with faint Red Group 44D on petal edges and tips. The base of each petal has on both surfaces a small (3/16×3/16 inch) Yellow-Orange Group 16B color spot. The major color on the upper side is Yellow-Orange Group 18B.

*Variegations.*—On guard petals there are occasional greenish-white stripes on both petal surfaces.

*Discoloration.*—The general tonality at the end of the first day: No change. At the end of the third day: No change. By day five, there is general fading to Yellow-Orange Group 18C. By day seven, fading is to Yellow-Orange Group 18D.

*Fragrance.*—Moderate, citrus.

Petals:

*Texture.*—Thick.

*Shape.*—Round.

*Form.*—Tips slightly recurved.

*Arrangement.*—Imbricated. Petaloids in the centr are few (zero to seven). Yellow-Orange Group 18B range from ¼ to ½ inch long and ⅛ to ¼ inch wide.

*Persistence.*—Petals drop off cleanly before drying.

*Lastingness.*—On the plant: Fair (about seven to eight days). As a cut flower: Fair (about eight to nine days).

Reproductive parts:

*Anthers.*—Size: Medium. Quantity: Many. Color: Yellow-Orange Group 21D. Arrangement: Regular around styles.

*Filaments.*—Color: Yellow-Orange Group 21D.

*Pollen.*—Present.

*Styles.*—Color: Red Group 53B.

*Stigmas.*—Color: Yellow-Orange Group 19C.

Plant:

*Form.*—Bush.

*Growth.*—Virogous, upright, branching, compact. At maturity, height is 3 to 3½ feet, width is 2 to 2½ feet.

Foliage: Number of leaflets on normal mid-stem leaves: Five.

*Size.*—Large (6 inches long×4½ inches wide).

*Quantity.*—Abundant.

*Color.*—New foliage: Upper and lower surfaces: Greyed-Orange Group 175A. Old foliage: Upper surface: Green Group 139A. Lower surface: Green Group 138B.

Leaflets:

*Shape.*—Oval.

*Texture.*—Leathery, glossy.

*Edge.*—Serrated.

*Serration.*—Single, small.

*Petiole rachis.*—Color: Green Group 138C on the lower surface. The upper surface is Greyed-Purple Group 183D.

*Petiole underside.*—Smooth, with occassional prickles.

*Stipules.*—Medium, serrated (about ⅝ inch), bearded.

*Disease resistance.*—Mildew and rust resistant under normal growing conditions, but susceptible to black-spot.

Wood:

*New wood.*—Color: Greyed-Orange Group 176B. Bark: Smooth.

*Old wood.*—Color: Green Group 137C. Bark: Smooth.

Prickles:

*Quantity.*—On main canes from base: Ordinary. On laterals from main canes: Ordinary.

*Form.*—Medium straight to hooked slightly upward.

*Color when young.*—Greyed-Orange Group 176B.

*Color when mature.*—Greyed-Orange 173D.

Small prickles:

*Quantity.*—On main stalks: None. On laterals: None.

I claim:

1. A new and distinct variety of rose plant of the floribunda class, substantially as herein shown and described, characterized particularly by a compact plant habit; dark green, glossy, disease-resistant foliage; abundant amber flowers; good clustering ability; and rapid rebloom.

* * * * *

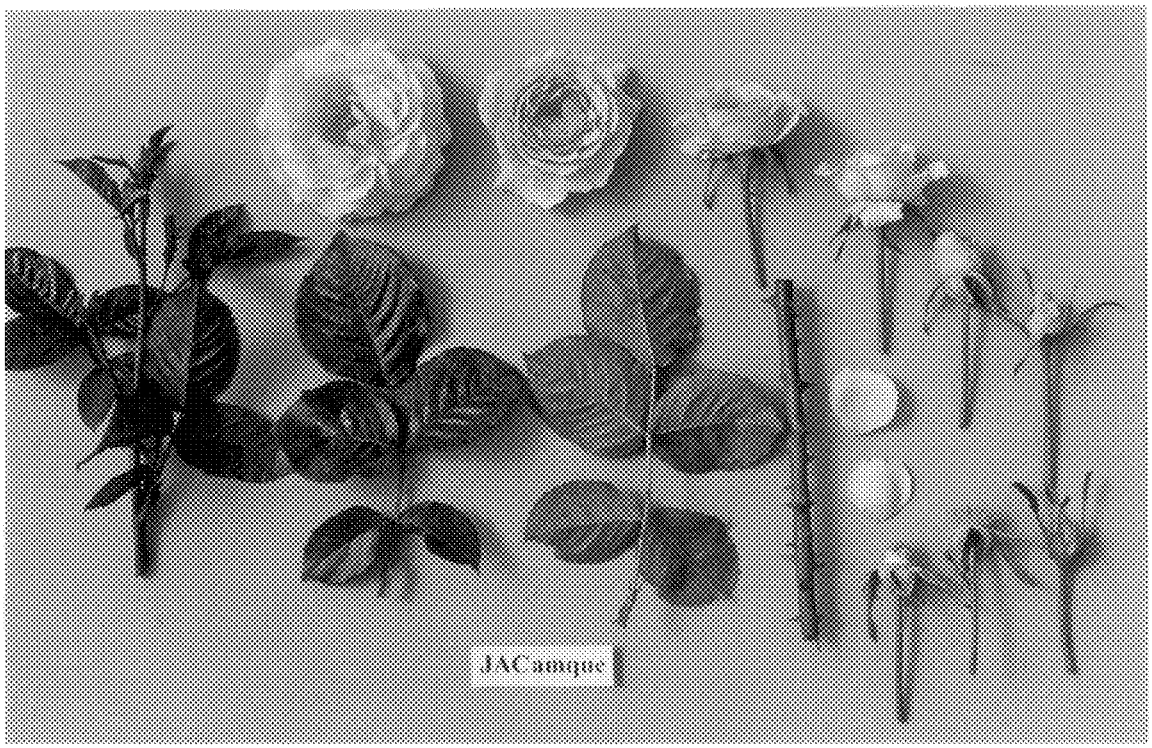
JACunique